United States Patent
Speer et al.

(10) Patent No.: US 7,980,512 B1
(45) Date of Patent: Jul. 19, 2011

(54) SYSTEM AND METHOD FOR DISPLAYING AERIAL REFUELING SYMBOLOGY

(75) Inventors: Thomas E Speer, Des Moines, WA (US); Joshua L Downs, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 659 days.

(21) Appl. No.: 12/139,032

(22) Filed: Jun. 13, 2008

(51) Int. Cl.
*B64D 39/00* (2006.01)
(52) U.S. Cl. ......................... 244/135 A; 345/8; 359/630
(58) Field of Classification Search .............. 244/135 A, 244/1 R; 340/971, 980, 973; 359/630, 839; 348/47, 56; 345/8, 9, 635, 419, 421; 701/3
See application file for complete search history.

(56) References Cited

U.S. PATENT DOCUMENTS

| | | | | |
|---|---|---|---|---|
| 4,093,347 A * | 6/1978 | La Russa | | 359/630 |
| 5,175,616 A * | 12/1992 | Milgram et al. | | 348/47 |
| 5,296,854 A * | 3/1994 | Hamilton et al. | | 345/9 |
| 5,499,784 A * | 3/1996 | Crabere et al. | | 244/135 A |
| 5,530,650 A | 6/1996 | Biferno et al. | | |
| 6,111,582 A * | 8/2000 | Jenkins | | 345/421 |
| 6,152,357 A | 11/2000 | Schintzer | | |
| 7,437,221 B2 * | 10/2008 | Hardman et al. | | 701/3 |
| 2005/0012684 A1 * | 1/2005 | Hewitt et al. | | 345/8 |
| 2006/0055628 A1 * | 3/2006 | Sanders-Reed et al. | | 345/8 |
| 2007/0242066 A1 * | 10/2007 | Levy Rosenthal | | 345/419 |
| 2008/0100570 A1 * | 5/2008 | Friedrich et al. | | 345/156 |

FOREIGN PATENT DOCUMENTS

| | | |
|---|---|---|
| EP | 1705116 | 9/2006 |
| EP | 1747992 | 1/2007 |
| FR | 2572706 | 5/1986 |
| FR | 2705082 | 11/1994 |

OTHER PUBLICATIONS

U.S. Appl. No. 11/090,347, filed Mar. 24, 2005, Perkins Cole.

* cited by examiner

*Primary Examiner* — Galen Barefoot
(74) *Attorney, Agent, or Firm* — Haynes and Boone, LLP

(57) ABSTRACT

In accordance with one or more embodiments, systems and methods for in-flight fuel delivery include an aerial refueling device adapted to provide fuel to a receiver aircraft, an optical component adapted to capture images of the aerial refueling device and the receiver aircraft, an operator input component adapted to interface with an operator and capture control signals as input from the operator, and a display component adapted to display images. A controller is adapted to receive the captured images and the captured control signals, process the control signals by generating graphic display symbology, process the images by generating a combined image having the generated graphic display symbology superimposed on the images, and display the combined image on the display component for viewing by the operator. The controller is adapted to superimpose the graphic display symbology on a portion of the images obscured by the aerial refueling device.

25 Claims, 13 Drawing Sheets

US 7,980,512 B1

SYSTEM AND METHOD FOR DISPLAYING AERIAL REFUELING SYMBOLOGY

TECHNICAL FIELD

The present disclosure relates generally to aerial refueling and, more particularly, to displaying aerial refueling symbology.

BACKGROUND

In the aviation industry, in-flight refueling extends the range and endurance of aircraft without requiring the aircraft to land. Although in-flight refueling is a relatively common operation, especially for military aircraft, the aircraft to be refueled (e.g., the receiver aircraft) must be precisely positioned relative to the tanker aircraft to provide safe engagement while the fuel is dispensed to the receiver aircraft. The precise relative spatial positioning of the two rapidly moving aircraft makes in-flight refueling a challenging operation.

One type of in-flight refueling system includes a boom refueling system that includes a rigid boom extending from the tanker aircraft, with a probe and nozzle at its distal end. The boom includes airfoils (e.g., rudders) controlled by a boom operator stationed on the refueling aircraft. The airfoils allow the boom operator to actively maneuver the boom with respect to the receiver aircraft, which usually flies in a fixed refueling position below and aft of the tanker aircraft. The boom operator typically monitors the aerial refueling boom with video displays to assist with guiding the boom nozzle into the receptacle of the receiver aircraft.

Conventional video displays provide essential information to the boom operator for readily cross-checking the status of the refueling system including boom elevation, azimuth, telescoping length, boom state, and fuel delivery without obscuring or otherwise losing sight of the receiver aircraft. Warning indicators are positioned so as to attract the boom operator's attention when concentrating on positioning the boom nozzle in the receiver aircraft's receptacle, without compromising safety by obscuring essential areas of the scene.

Some conventional video displays provide visual overlays of this essential information in the form of linear scales, numeric fields, and warning indicators that are displayed at fixed locations in the displayed images. Generally, the visual overlays displayed over the images of the receiver aircraft obscure the boom operator's view of the receiver aircraft during the aerial refueling process, which is typically unsafe. In some instances, conventional overlays may obscure dangerous situations in aerial refueling, which may increase the occurrence of damage to the aerial refueling boom and receiver. As a result, there is a need for an improved system and method for providing visual overlays in displayed images of aerial refueling operations that improve safety.

SUMMARY

Systems and methods disclosed herein, in accordance with one or more embodiments, provide for overlaying or superimposing graphic display symbology on a displayed image, such as a photographic scene of an aerial refueling operation between a tanker aircraft and a receiver aircraft. The graphic display symbology provides an operator with information on position, status, and cautions/warnings of an aerial refueling device. The graphic display symbology presents information to an operator in an easily viewable form, reduces interference with viewing receiver aircraft, and provides warning indications within the operator's field of view (e.g., primary field of view).

In accordance with one or more embodiments, a system for in-flight fuel delivery includes an aerial refueling device adapted to provide fuel to a receiver aircraft, an optical component adapted to capture images of the aerial refueling device and the receiver aircraft, an operator input component adapted to interface with an operator and capture control signals as input from the operator, and a display component adapted to display images. The system includes a controller adapted to receive the captured images and the captured control signals, process the control signals by generating graphic display symbology, process the images by generating a combined image having the generated graphic display symbology superimposed on the images, and display the combined image on the display component for viewing by the operator. The controller is adapted to superimpose the graphic display symbology on a portion of the images obscured by the aerial refueling device. The controller is adapted to process the control signals by determining a position of the aerial refueling device.

In various implementations, the controller is adapted to dynamically position the graphic display symbology over the portion of the images obscured by the aerial refueling device as the aerial refueling device moves in the images. The aerial refueling device includes a boom component and at least one rudder component having physical markings on a portion thereof. The controller superimposes the graphic display symbology on a portion of the image proximate to the physical markings. The optical components include stereoscopic cameras adapted to have a field of view of at least one of the aerial refueling device and the receiver aircraft, and the graphic display symbology is superimposed over the image in the field of view.

In various implementations, the graphic display symbology includes a plurality of chevron symbols that define a boom envelope in the image. The chevron symbols may be positioned at corners of the boom envelope. The chevron symbols may be sized and/or positioned for a specific type of receiver aircraft and boom extension. The graphic display symbology includes a center symbol positioned at a center of the boom envelope. The graphic display symbology includes a plurality of position indicators that provide position information related to the aerial refueling device including at least one of an elevation position, an azimuth position, and a telescoping position. The graphic display symbology includes warning indicators and status indicators that are displayed in the image with a semi-transparent pixel mask to avoid obscuring the aerial refueling device or the receiver aircraft. The graphic display symbology includes a force cue, such as an arrow superimposed on a portion of the aerial refueling device. The arrow defines a direction of projected force on a nozzle component of the aerial refueling device. The graphic display symbology includes a master caution indicator and a master warning indicator superimposed on a portion of the aerial refueling device. The master caution indicator comprises a yellow color to indicate a master caution state, and the master warning indicator comprises a red color to indicate a master warning state.

In various implementations, the graphic display symbology includes graphic position gauges and refueling status lights that are displayed over and track the position of at least one of a boom component and a rudder component in the images of the aerial refueling device. The graphic position gauges provide position information related to the aerial refueling device including at least one of an elevation position of the boom component, an azimuth position of the boom component, and an extension position of the boom tip component. One or more refueling status indicators provide an indication of a refueling status including but not limited to the terms Ready, Contact, and Disconnect.

In accordance with one or more embodiments, a method for in-flight fuel delivery from a tanker aircraft to a receiver aircraft via an aerial refueling device includes receiving images from an optical component, the images having a field of view of at least one of the aerial refueling device and the receiver aircraft and receiving control signals from an operator input component. The method includes processing the control signals by generating graphic display symbology and processing the images by generating a combined image having the generated graphic display symbology superimposed on the images. The method includes displaying the combined image on a display component. The graphic display symbology is superimposed on a portion of the images obscured by the aerial refueling device.

The scope of the disclosure is defined by the claims, which are incorporated into this section by reference. A more complete understanding of embodiments is afforded to those skilled in the art, as well as a realization of additional advantages thereof, by a consideration of the following detailed description of one or more embodiments. Reference is made to the appended sheets of drawings as described in greater detail herein.

BRIEF DESCRIPTION OF THE DRAWINGS

Embodiments and their advantages are best understood by referring to the detailed description that follows. It should be appreciated that like reference numerals are used to identify like elements illustrated in one or more of the figures.

DETAILED DESCRIPTION

In accordance with one or more embodiments of the present disclosure, systems and methods disclosed herein provide for overlaying graphic display symbology on a displayed image, such as a photographic scene, to provide an operator with information on position, status, and cautions/warnings of an aerial refueling device. The graphic display symbology includes a plurality of graphical symbols related to the aerial refueling operation and presents information to an operator in an easily viewable form, reduces interference with viewing receiver aircraft, and provides warning indications within the operator's field of view (e.g., primary field of view). In one implementation, as described in greater detail herein, the symbology may be superimposed on portions of the scene. In other implementations, tracking of the aerial refueling device may operate in conjunction with physical markings on the underside of the boom to avoid obscuring the operator's view of receiver aircraft. As such, the graphic display symbology provides an operator with essential information for monitoring and controlling aerial refueling. For example, the graphic display symbology displayed over one or more components of a boom provides easily viewable information close to a center of the operator's field of view during pre-contact and contact phases of air refueling while maximizing the available unobstructed view of the receiver aircraft.

In accordance with one or more embodiments of the present disclosure, systems and methods disclosed herein are capable of displaying boom position (e.g., elevation angle, azimuth angle, and telescoping length), fuel system state (e.g., ready/contact/disconnect), and warnings, cautions, and alerts superimposed on images of an aerial refueling display. In various implementations, the position of data and information in the displayed field of view is varied continuously so as to superimpose the symbols on the displayed image of the aerial refueling boom in the field of view. As such, essential data and information are provided in an operator's field of view without obscuring the operator's view of the receiver aircraft. In one aspect, the overlays operate in concert with markings on the aerial refueling boom to provide the operator with analog indication of the boom's angular position with respect to the contact, disconnect and mechanical envelopes.

Figure 1A:
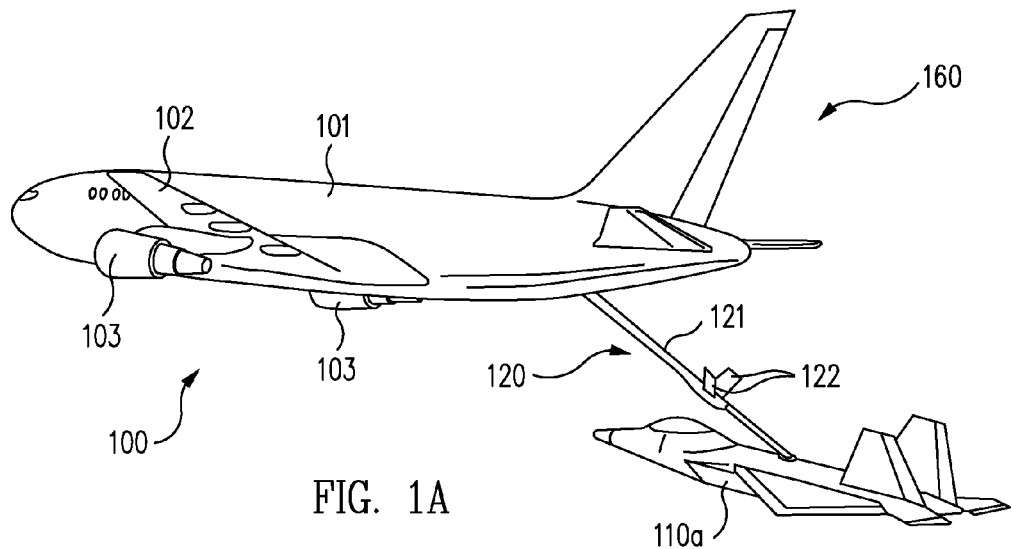
FIG. 1A shows a tanker aircraft refueling a receiver aircraft, in accordance with an embodiment of the present disclosure.

FIG. 1A shows one embodiment of an aerial refueling system 160 comprising a tanker aircraft 100 refueling a receiver aircraft 110a with an aerial refueling device 120. As shown in FIG. 1A, the tanker aircraft 100 includes a fuselage 101, one or more wings 102, and one or more engines 103. In various other embodiments, the aircraft 100 may include various other types of configurations.

The aerial refueling device 120, in one embodiment, may include a refueling boom 121 having one or more actuatable control components 122 (e.g., rudders). The positions of the control components 122 may be adjusted to steer the boom 121 into engagement with the receiver aircraft 110a. The position of the boom 121 may be controlled based on inputs received via one or more sensors and/or inputs received from a human operator. The aerial refueling device 120 may be configured to allow the operator to manually control the boom 121 and/or may allow the system 160 to automatically control the boom 121, either separately or simultaneously. In one implementation, the operator may control the location of the boom 121 with assistance from the automatic portion of the system 160, while allowing the operator to override the automatic portion of the system 160 at any point.

Figure 1B:
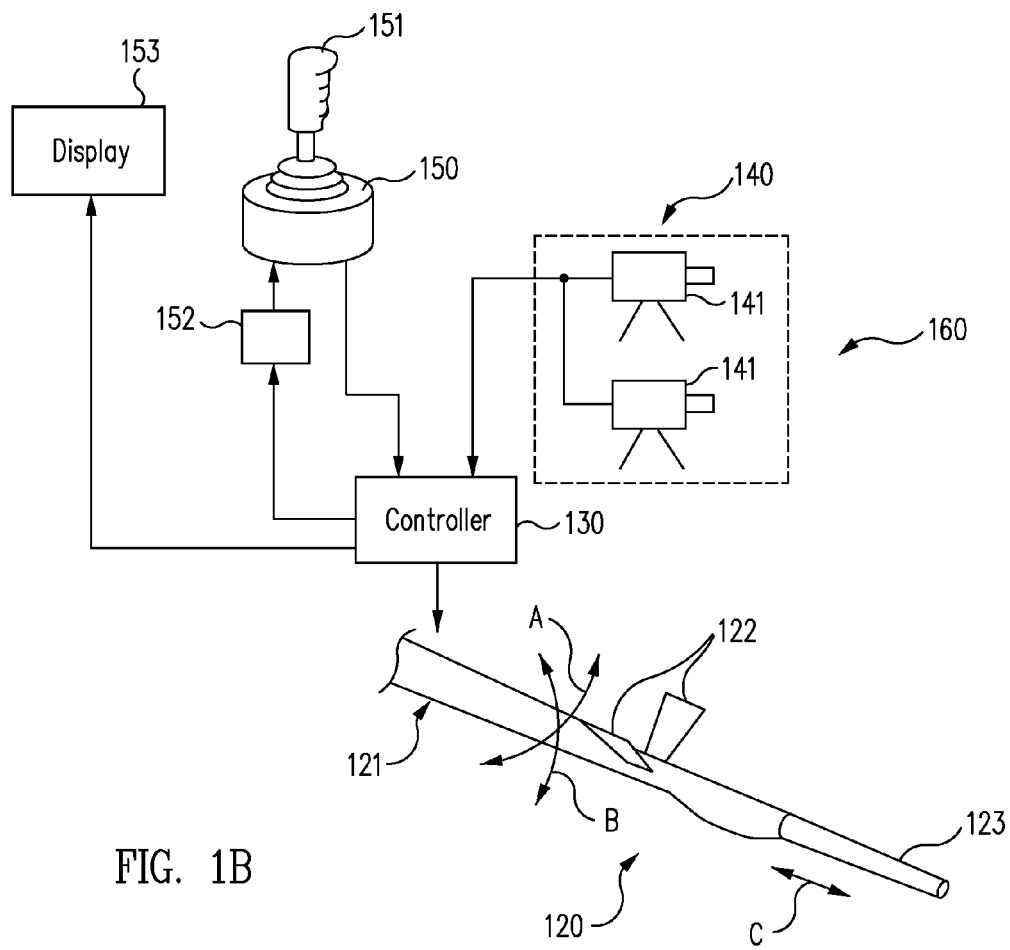
FIG. 1B shows a system for controlling an aerial refueling device, in accordance with an embodiment of the present disclosure.

FIG. 1B shows one embodiment of a plurality of components of the system 160 in reference to FIG. 1A. As shown in FIG. 1B, the system 160 includes a controller 130 adapted to control the motion of the aerial refueling device 120, based on inputs received from an operator input device 150 and one or more sensor 140. The operator input device 150, in one embodiment, may include a stick 151 or various other types of manual input control device (e.g., a yoke). Each sensor 140, in one embodiment, may include an optical sensor, such as one or more photosensitive detectors 141 (e.g., a pair of cameras) that provide a stereoscopic image to the controller 130. The controller 130, in one embodiment, may receive input signals from the one or more sensors 140 and the operator input device 150 and, based upon a combination of the input signals, direct a command signal to the aerial refueling device 120 to change and/or alter a position of the aerial refueling device 120.

Referring to FIG. 1B, the controller 130 is adapted to direct actuation of the control components 122 to provide for lateral motion of the boom 121, as indicated by arrow A, and vertical or pitch motion of the boom 121, as indicated by arrow B. The controller 130 is adapted to control axial actuation (e.g., extension, such as telescoping extension) of a deployable boom tip 123, as indicated by arrow C. In one implementation, an actuator 152 may be coupled between the controller 130 and the operator input device 150 to provide feedback to the operator. In one example, when the controller 130 directs a command signal to move the boom 121 to a particular position, a corresponding command signal may be directed to the actuator 152 to move the operator input device 150 in a corresponding position. When placing a hand lightly on the stick 151, the operator may sense the stick 151 move in a manner that tracks the motion of the boom 121 and/or in a manner that is commanded by the controller 130 based on input from the one or more sensors 140. As such, if the operator places any force (e.g., greater than a threshold level of force) on the stick 151, the operator input to the stick 151 may influence the position of the boom 121. Hence, in one aspect, the rate at which the controller 130 directs a motion of the boom 121 based on the operator input, may vary proportionately to the force applied by the operator to the operator input device 150.

Referring to FIG. 1B, the controller 130, in one embodiment, is adapted to display images from the one or more sensors 140 (e.g., one or more image or video cameras) on a display component 153 for viewing by the operator. The controller 130 may be adapted to display a field of view that includes the receiver aircraft 110a and the aerial refueling device 120 on the display component 153. In another embodiment, the controller 130 is adapted to graphically display operator input from the operator input device 150. For example, the controller 130 may be adapted to superimpose graphics on the displayed images for viewing by the operator. In various implementations, the graphics may include control graphics that indicate positions of the aerial refueling device 120, including the boom 121, the control components 122 and various other components thereof. These display graphics including the control graphics are described in greater detail herein. Further scope and operation related to controlling aircraft refueling may be found in co-pending U.S. Patent Application entitled, "SYSTEMS AND METHODS FOR AUTOMATICALLY CONTROLLING AIRCRAFT REFUELING," Ser. No. 11/090,347, filed Mar. 24, 2005, which is hereby incorporated by reference in its entirety.

Figure 1C:
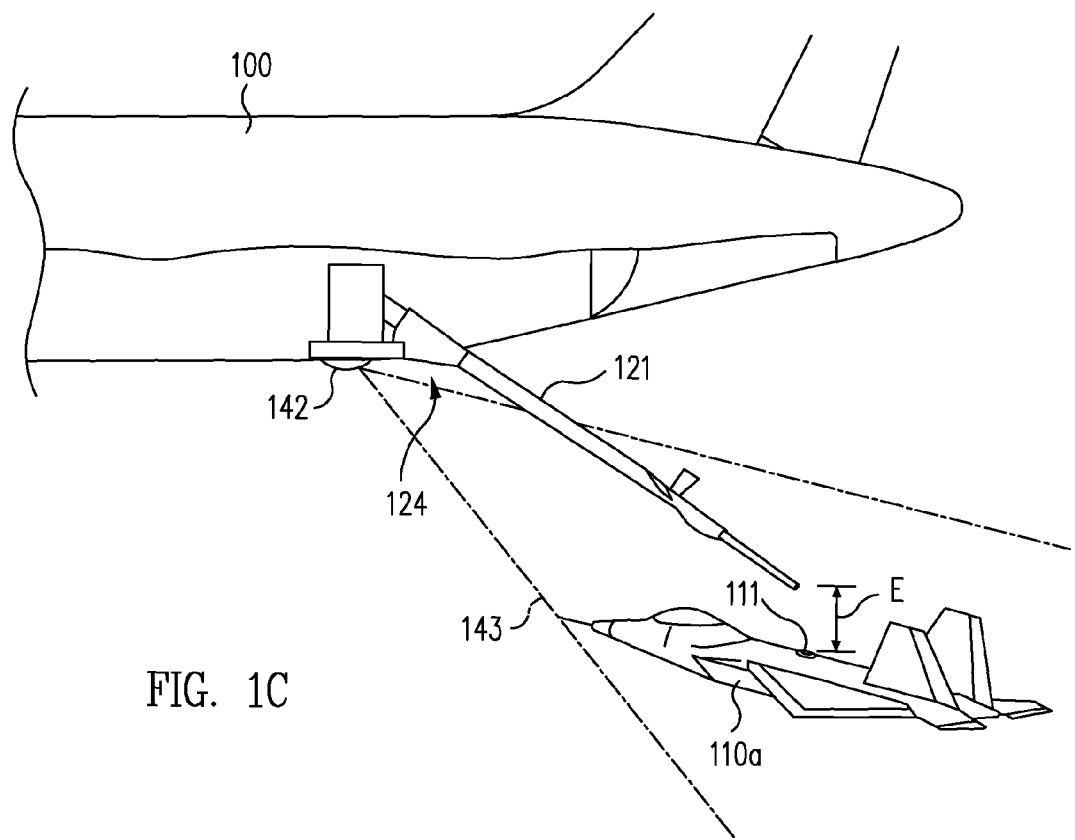
FIG. 1C shows a field of view (FOV) of a tanker aircraft refueling a receiver aircraft, in accordance with an embodiment of the present disclosure.

FIG. 1C shows one embodiment of a partially cut away side view of the tanker aircraft 100 refueling the receiver aircraft 110a. As shown in FIG. 1C, a sensor pod 142 houses the one or more sensors 140 of FIG. 1B at a location where the one or more sensors 140 may detect the position of the boom 121 and the receiver aircraft 110a. In one implementation, the one or more sensors 140 is adapted to have a sensor field of view 143 that extends downwardly and aft from the sensor pod 142. The one or more sensors 140 within the sensor pod 142 is adapted to detect a position of at least one of the receiver aircraft 110a and the boom 121 so as to determine a position error E. For example, the position error E may include the vector distance between the tip of the boom 121 and a refueling receptacle 111 of the aircraft and may include position components in a plurality of coordinate directions (e.g., azimuth, elevation, and extension such as telescoping position). The controller 130, in one embodiment, is adapted to display images from the field of view 124 of the one or more sensors 140 (e.g., one or more image detectors) on the display component 153 for viewing by the operator. In various implementations, the displayed images of the field of view 124 may include display graphics that provide information related to the position of the aerial refueling device 120 and the various components thereof including the boom 121, the control components 122 and the telescoping boom tip 123. The display graphics including various aspects thereof are described in greater detail herein.

Figure 1D:
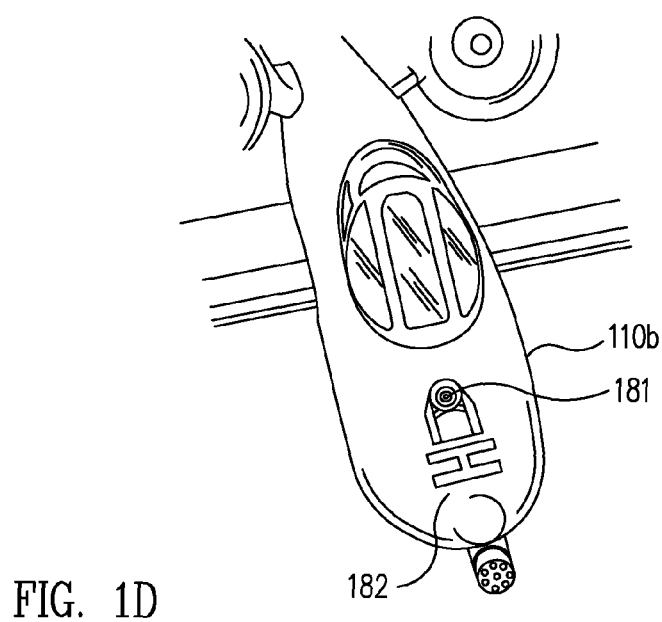
FIG. 1D shows a receiver aircraft, in accordance with an embodiment of the present disclosure.

FIG. 1D shows one embodiment of a receiver aircraft 110b with one suitable position for a fuel receptacle 181. The fuel receptacle 181 may include a distinctive visual appearance and/or may include visual cue markings 182 that assist the one or more sensors 140 in precisely identifying the location of the fuel receptacle 181. In one implementation, the one or more sensors 140 may be used to optically determine the distance between the boom tip 111 and the receptacle 182. In another embodiment, the boom 121 may include a separate position sensor (e.g., an accelerometer with a processor), and the position detected by the boom position sensor may be combined with the visual image of the fuel receptacle 181 to determine the distance between the boom tip 111 and the fuel receptacle 181.

Figure 2A:
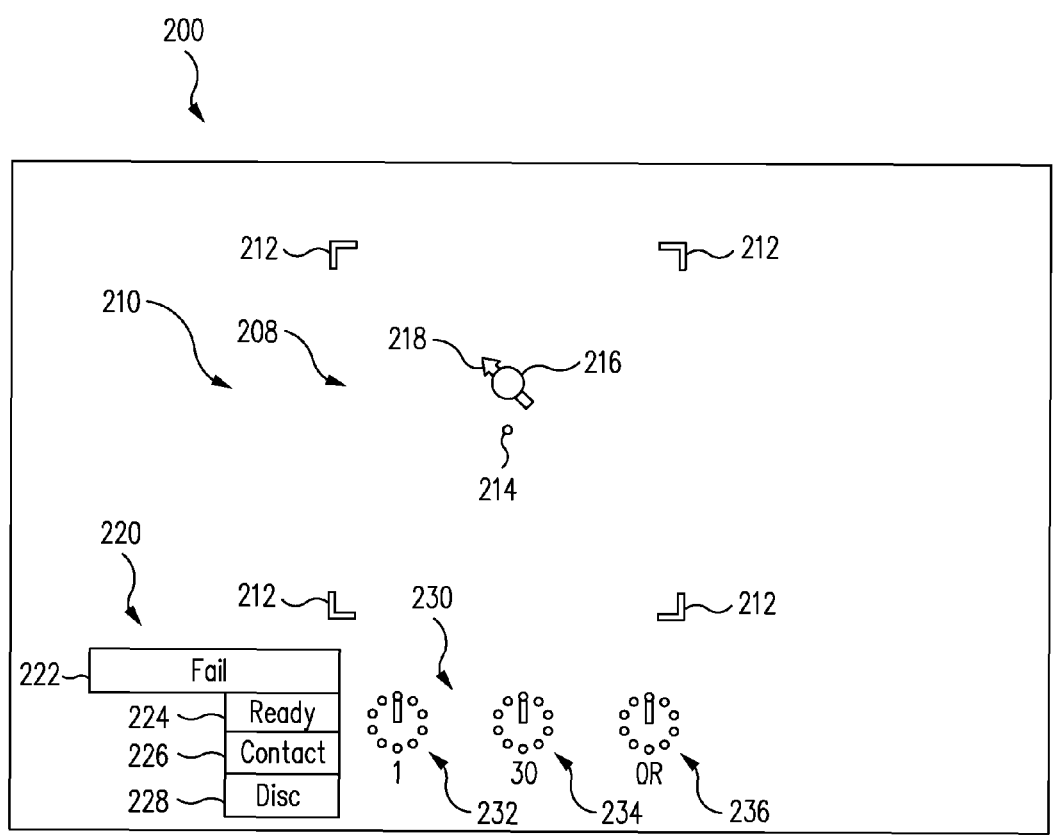
FIGS. 2A-2B show various FOV displays having graphic display symbology, in accordance with one or more embodiments of the present disclosure.

FIG. 2A shows one embodiment of a field of view (FOY) display 200 having graphic display symbology 210 including a plurality of chevron symbols 212, a center symbol 214, a master warning/caution indicator 216, a force cue 218, a plurality of status indicators 220, and a plurality of position indicators 230. The chevron symbols 212, in one embodiment, mark four corners of a disconnect envelope, which identify a boom envelope 208 (e.g., frame of control). In various implementations, the chevron symbols 212 may be sized and/or positioned for a specific type of receiver aircraft and boom extension. The center symbol 214, in one embodiment, identifies the central region of the boom envelope 208 as identified by the chevrons 212.

The master warning/caution indicator 216, in one embodiment, is positioned proximate to the central region of the boom envelope 208. In this position, the master warning/caution indicator 216 is easily viewable by an operator for immediate indication of an alert, a caution or a warning. In various implementations, the master warning/caution indicator 216 comprises a red color to indicate a master warning state and a yellow color to indicate a master caution state. The force cue 218, in one embodiment, identifies the direction of force on the aerial refueling device 120 so that the operator may steer or maneuver the aerial refueling device 120 in a corrective or compensating manner.

The status indicators 220, in one embodiment, identify various information related to the "state of the fuel system" of the aerial refueling device 120 and include a fail status indicator 222, a ready status indicator 224, a contact status indicator 226, and a disconnect status indicator 228. In various implementations, as shown in FIG. 2A, the status indicators 230 comprise a semi-transparent rectangular graphic with alphanumeric characters that provide the operator with easily viewable information about the status (e.g., fuel system state) of the aerial refueling device 120. In one example, the warning and status indicators are displayed with a pixel mask that allows the underlying image to show through, which may avoid obscuration of the visual scene.

The fail status indicator 222, in one embodiment, indicates to the operator that the aerial refueling device 120 is positioned outside the boom envelope 208, as indicated by the chevrons 212. The ready status indicator 224 indicates to the operator that the aerial refueling device 120 is ready for operation including steering and maneuvering. The contact status indicator 226 indicates to the operator that the aerial refueling device 120 is in contact with the receiver aircraft 110a, for example, as shown in FIG. 1A. The disconnect status indicator 228 indicates to the operator that the aerial refueling device 120 is disconnected from the receiver aircraft 110a, which may be indicated after refueling of the receiver aircraft 110a has been completed.

The position indicators 230, in one embodiment, identify positions of the aerial refueling device 120 and include an elevation position indicator 232, an azimuth position indicator 234, and an extension (e.g., telescoping) position indicator 236. In one implementation, as shown in FIG. 2A, the position indicators 230 include a circular arrangement of multi-dot circles and a data component (e.g., alphanumeric component) to identify a particular degree of orientation in elevation (el) 232, azimuth (az) 234, and telescope (tel) 236. The multi-dot circles (e.g., 10-dot circles) are used for numeric scales to reduce their area in the field of view and to provide improved trend information. The position indicators 230 may include a hand that rotates clockwise and/or counter-clockwise to visually indicate the degree of orientation in reference to the data component.

The elevation position indicator 232 identifies the degree of elevation movement of the boom 121 of the aerial refueling device 120, as described in reference to the vertical or pitch motion of the boom 121 by arrow B in FIG. 1B. The azimuth position indicator 234 identifies the degree of azimuth movement of the boom 121 of the aerial refueling device 120, as described in reference to the lateral motion of the boom by arrow A of FIG. 1B. The extension or telescoping position indicator 236 identifies the degree of axial movement of the boom tip 123 from the boom 121 of the aerial refueling device 120, as described in reference to the extending or telescoping motion of the boom tip 123 by arrow C of FIG. 1B.

Figure 2B:
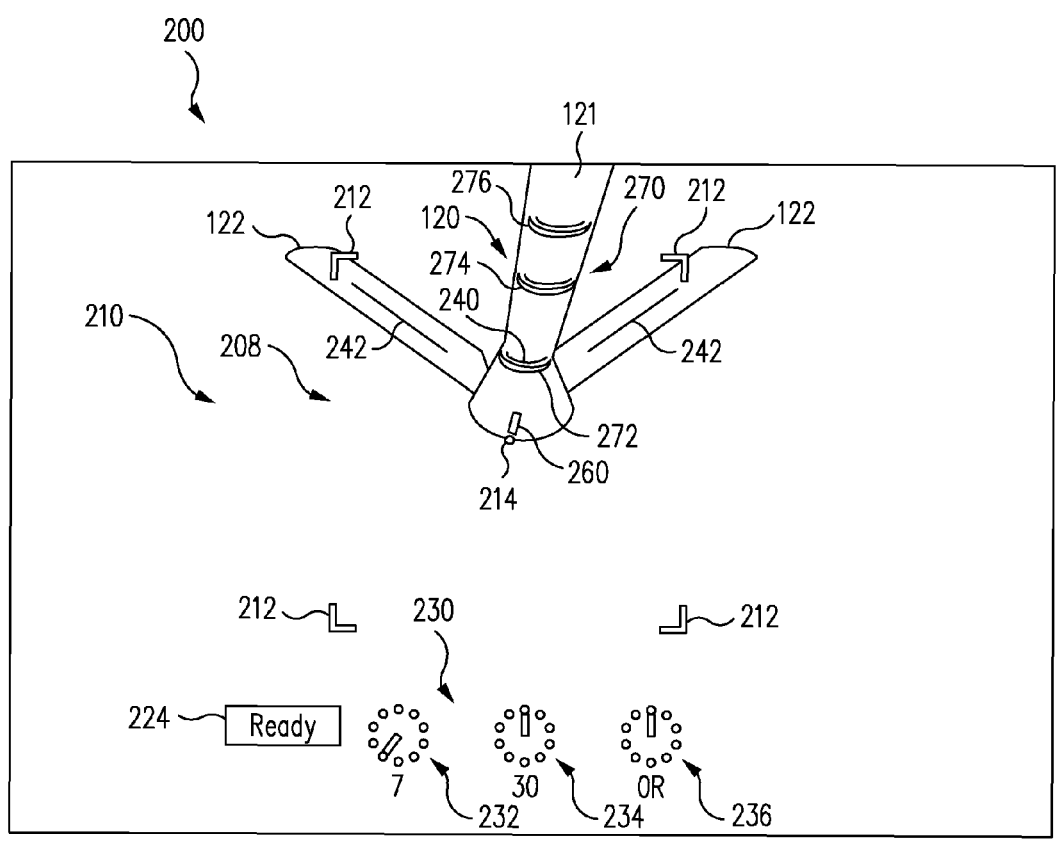

FIG. 2B shows one embodiment of another field of view display 250 having graphic display symbology 210 including the chevrons 212, the center symbol 214, the ready status indicator 224, and the position indicators 232, 234, 236. As shown in FIG. 2B, the field of view 250 includes an image of the aerial refueling device 120 with portions of the boom 121 and the control components 122 (e.g., rudders) within the boom envelope 208, as provided by the chevrons 212. In one aspect, the ready status indicator 224 informs an operator that the aerial refueling device 120 is properly positioned and ready for use.

The field of view display 250, in one embodiment, includes a stripe 260 superimposed on the image of the boom 121 that parallels an angular orientation of the boom 121. In one implementation, as shown in FIG. 2B, the stripe 260 is adapted to track the angle of the boom 121, along its length, to provide an operator with an easily viewable graphic for immediate indication of the angular orientation of the boom 121.

The field of view display 250, in one embodiment, includes one or more elevation indicators 270 superimposed on the image of the boom 121. In various implementations, a first elevation indicator 272 identities a first elevation of the boom 121, such as a 35° el, and a second elevation indicator 274 identities a second elevation of the boom 121, such as a 40° el, and a third elevation indicator may identity a third elevation of the boom 121, such as a 50° el., which is the mechanical boundary of the boom 121.

Referring to FIG. 2B, physical markings on the boom 121 may include one or more transverse stripes 240 on the boom 121 and one or more fiducial marks 242 on the housing of the control components 122. Examples of fixed symbols displayed on the image include a dot at the center (e.g., center symbol 214) and the chevrons 212 marking the corners of the disconnect envelope (e.g., boom envelope 208). In various implementations, the symbols are positioned on the stereoscopic images such that they appear to be at the same distance as the length of the structural tube of the boom 121. For example, when the bottom of the fiducial mark on the boom 121 is coincident with the center symbol 214, the boom 121 is positioned at the center of the boom envelope 208 (e.g., 30° el and 0° az). As the boom 121 approaches a boundary of the boom envelope 208, one or more chevrons 212 enter into the operator's area of concentration, which provides, for example, an immediate and intuitive indication of how far the boom 121 may move before reaching the boundary.

The field of view display 250, in one embodiment, includes quantitative boom position information, as provided by the multi-dot circles of the position status indicators 232, 234, 236 at the bottom of the display. In various aspects, trend information are readily viewable by the operator's peripheral vision, and the indicators 232, 234, 236 are readily viewable such that all three may be perceived at a glance. In one aspect, an under-running receiver aircraft 110a, 110b may bring the elevation status indicator 232 within the operator's area of concentration, thereby reinforcing the need to disconnect immediately.

The field of view display 250, in one embodiment, provides boom status and warning indicators 222, 224, 226, 228 (FIG. 2A), which are displayed in a semi-transparent manner so as to not overly obscure the operator's view of the receiver aircraft 110a, 110b when the receiver aircraft 110a, 110b is in an extreme position relative to the tanker aircraft 100. As such, when a new warning, caution or alert occurs, the warning indicator 216 (FIG. 2A) may be displayed superimposed on a portion of the boom 121. This warning indicator 216 is positioned to immediately alert the operator to view the status area for more information as to the cause of the warning indication. For example, positioning the warning indicator 216 at an end of the boom 121, which is in the operator's area of concentration, reduces the probability of missing the onset of the alert. Since the boom 121 may physically obscure the view of the receiver aircraft 121, this does not interfere with the operator's ability to position the boom 121 in the receptacle 181 of the receiver aircraft 110b of FIG. 1D or maintain a proper clearance from the receive aircraft 110b.

FIGS. 3A-3E show various exemplary embodiments of the aerial refueling device 120 in the fields of view 200, 250 of the display component 153. In various implementations, FIGS. 3A-3E show combinations of symbols having fixed locations, symbols that are superimposed on a boom image, and reference markings painted on the boom itself for tracking positions of the boom as it moves in the displayed images.

Figure 3A:
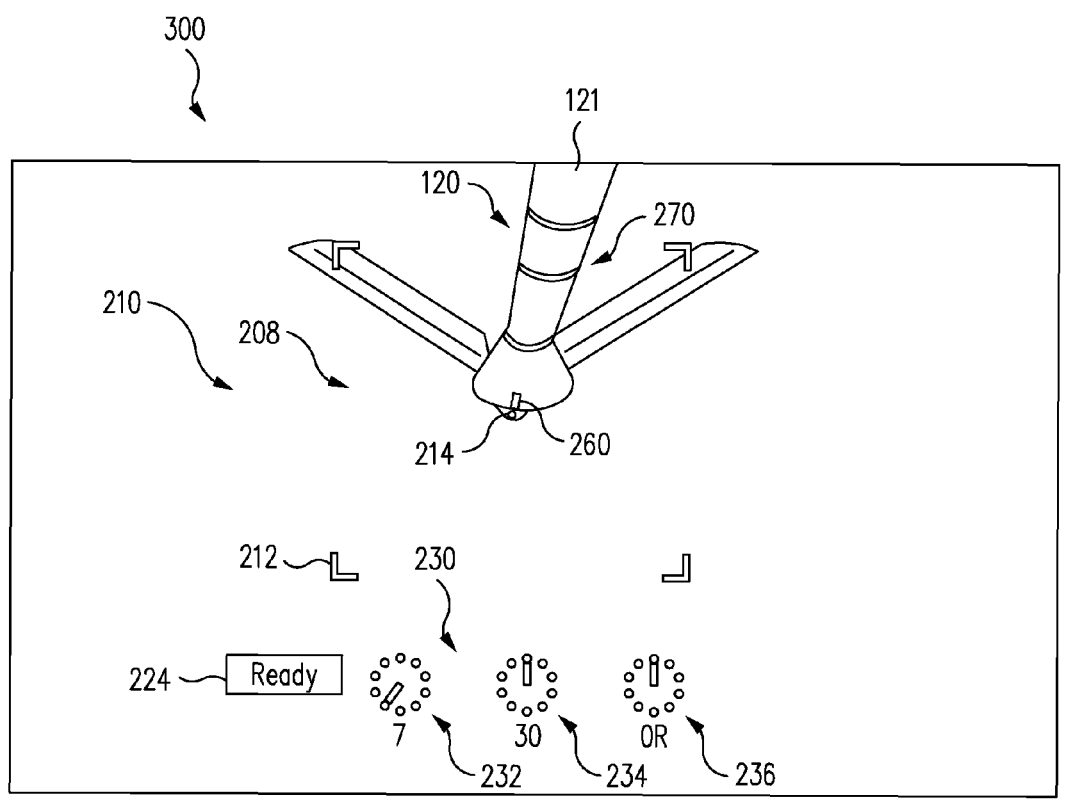
FIGS. 3A-3E show various exemplary embodiments of an aerial refueling device in various FOV displays having graphic display symbology, in accordance with one or more embodiments of the present disclosure.

FIG. 3A shows one embodiment of a field of view 300 displaying a photographic image of the aerial refueling device 120, as displayed by the system 160 and seen from an operator in-flight. The field of view 300 includes an image of the aerial refueling device 120 with portions of the boom 121 and the control components 122 within the boom envelope 208, as provided by the chevrons 212. As shown in FIG. 3A, the boom 121 is positioned at the center of the refueling envelope (e.g., boom envelope 208) with the telescoping boom tip 123 retracted. In one implementation, the ready status indicator 224 informs an operator that the aerial refueling device 120 is properly positioned and ready for use.

Figure 3B:
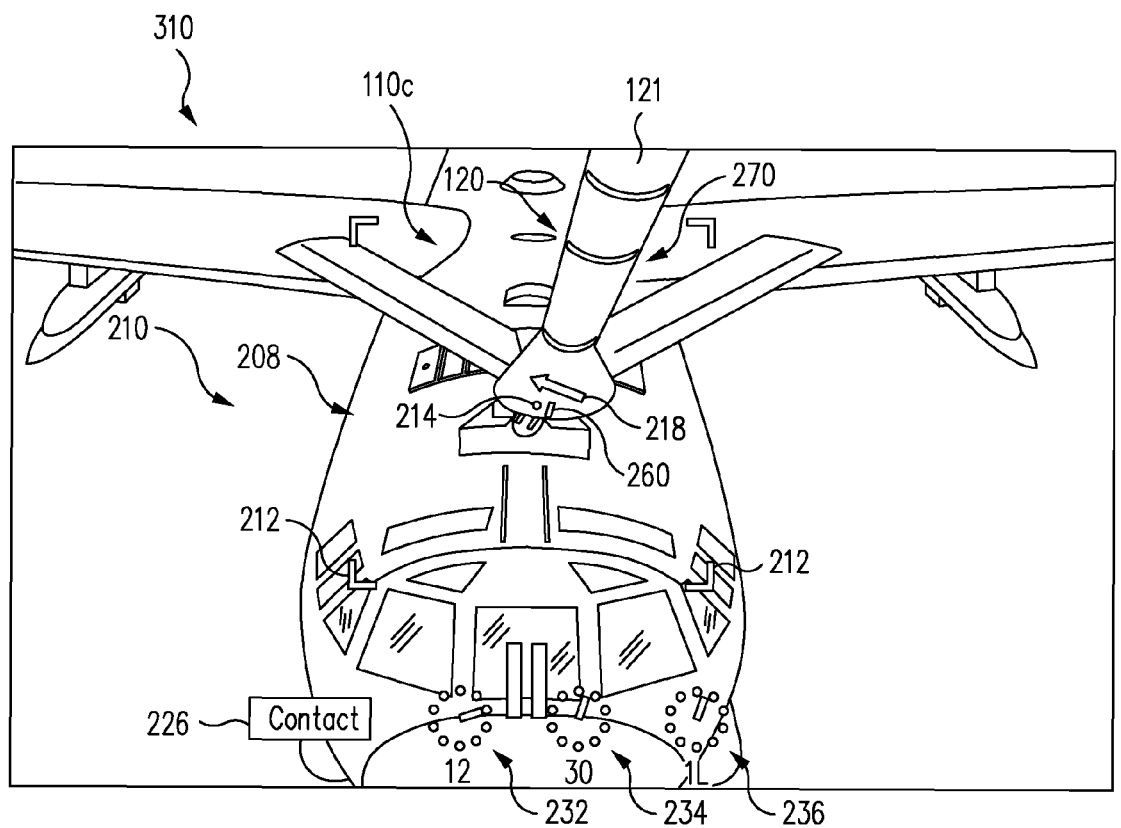

In various embodiments, the aerial refueling boom 121 is an object of visual interest for an operator as the operator maneuvers the boom 121 in the vicinity of a receiver aircraft. Therefore, indicators that appear to be mounted to the boom 121 are provided in the operator's area of attention. Since the boom 121 may obscure part of the view of the receiver aircraft, superimposing the symbols on the boom 121 may not subtract from the view of the receiver aircraft by the operator. Physical markings on the boom 121 are adapted to operate in conjunction with symbols fixed in the field of view of the vision system 160 to provide an intuitive, analog indication of boom angular position. Symbols are not fixed in the field of view, but are adapted to move dynamically with the aerial refueling boom 121. Symbols are not displayed at a fixed apparent distance or viewing plane, but are adapted to be located at a radius of the boom 121, which may obviate any need for the operator to change a focus of depth perception. Markings may be added to the boom 121 that provide the boom with an indicator, as part of the display system 160. These and other aspects of the present disclosure are described in greater detail herein FIG. 3B shows one embodiment of another field of view 310 displaying another photographic image of the aerial refueling device 120, as displayed by the system 160 and seen from an operator in-flight. As shown in FIG. 3B, the field of view 310 includes an image of a receiver aircraft 110c and an image of the aerial refueling device 120 in contact with the receiver aircraft 110c, as indicated by the contact status indicator 226. In one aspect, the contact status indicator 224 informs an operator that the aerial refueling device 120 is properly connected to the receiver aircraft 110c and ready for refueling.

In one implementation, referring to FIG. 3B, the boom 121 is coupled to the receiver aircraft 110c. When in contact, the force cue 218 comprises an arrow superimposed on the image of the boom 121 and indicates a direction of force being applied to the boom nozzle, as measured by one or more sensors, such as an Automatic Load Alleviation System (ALAS) sensors. This allows the operator to monitor ALAS performance. Moving the boom 121 in the direction of the force cue arrow 218 will manually alleviate the nozzle load. In one example, the force cue arrow 218 is green when the load is within a normal tolerance (e.g., <500 lb), yellow when the load is elevated, and red when excessive. In another example, the force cue arrow 218 is not shown when the boom 121 is disconnected from the receiver aircraft 110c, which would provide a redundant indication of boom status.

Figure 3C:
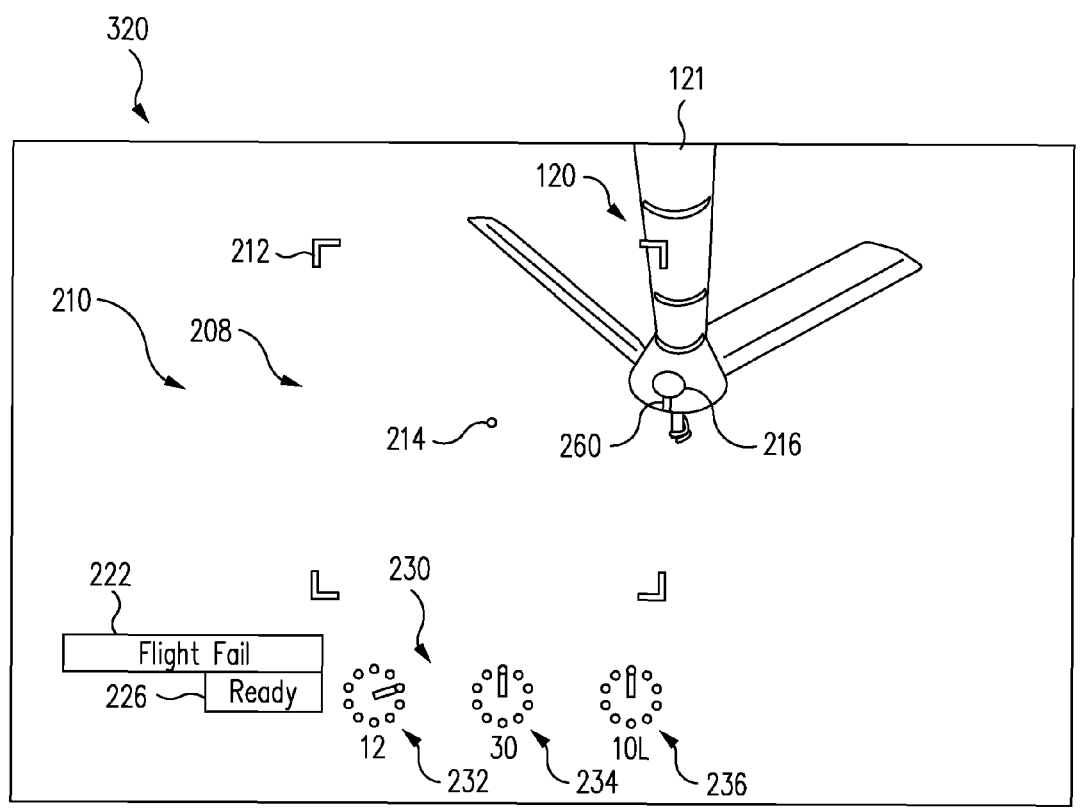

FIG. 3C shows one embodiment of another field of view 320 displaying another photographic image of the aerial refueling device 120, as displayed by the system 160 and seen from an operator in-flight. As shown in FIG. 3C, the field of view 320 includes an image of the aerial refueling device 120 with portions of the boom 121 and the control components 122 outside the boom envelope 208, as indicated by the fail status indicator 222 and the warning indicator 216, which is positioned at a lower part of the boom 121.

In one implementation, referring to FIG. 3C, the boom 121 is positioned at a side boundary of the disconnect envelope (e.g., boom envelope 208). The warning indicator 218 is red (e.g., indicating a master warning) and superimposed on an end of the boom 121 with a corresponding warning message in the warning status indicator 222. Also, the azimuth position indicator is red because the boom 121 is outside the boom envelope 208.

In one aspect, even though the ready status indicator 224 indicates ready for use, the fail status indicator 222 informs an operator that the aerial refueling device 120 is not properly positioned within the boom envelope 208 and, as such, is not ready for use. In another aspect, the "flight fail" text, as displayed by the fail status indicator 222, informs an operator that the control components 122 of the aerial refueling device 120 have steered the boom 121 to a position outside the boom envelope 208. Thus, for corrective maneuvering, the operator should counter steer (e.g., fly) the boom 121 to a proper position within the boom envelope 208 (e.g., as shown in FIG. 3A).

Figure 3D:
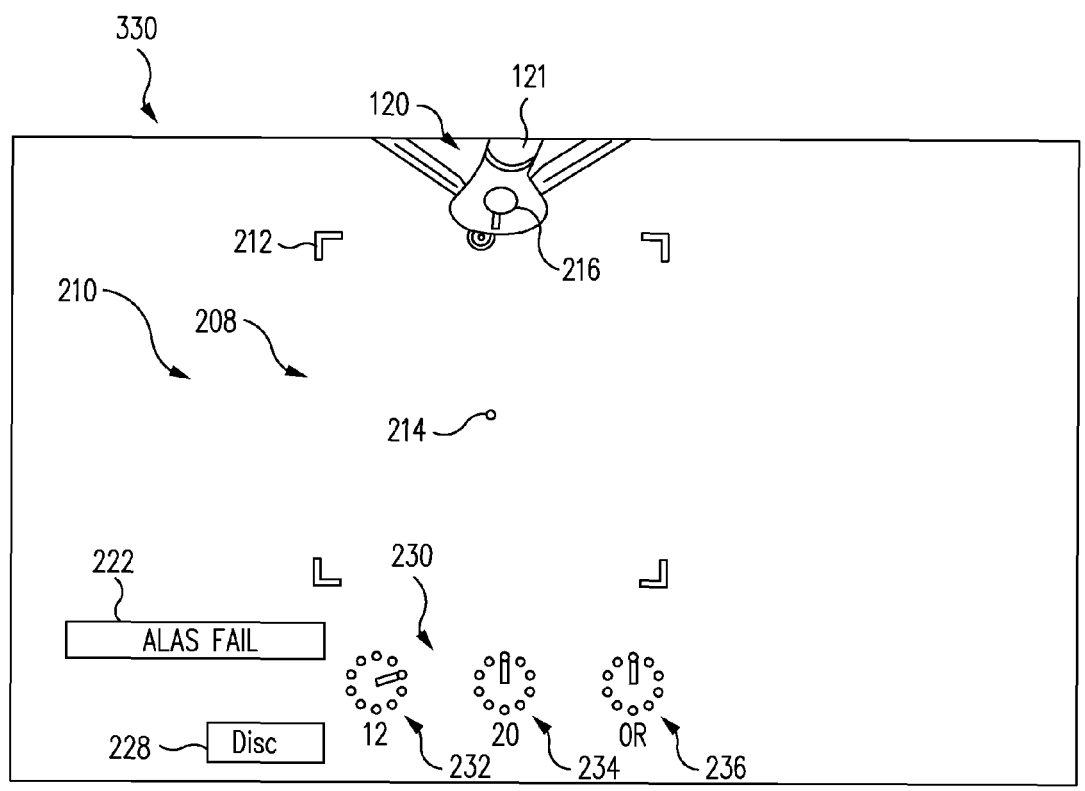

FIG. 3D shows one embodiment of another field of view 330 displaying another photographic image of the aerial refueling device 120, as displayed by the system 160 and seen from an operator in-flight. As shown in FIG. 3D, the field of view 330 includes an image of the aerial refueling device 120 with portions of the boom 121 and the control components 122 outside the boom envelope 208, as indicated by the fail status indicator 222 and the warning indicator 216, which is positioned at a lower part of the boom 121.

In one implementation, referring to FIG. 3D, the warning indicator 216 is yellow (e.g., indicating a master caution) and superimposed on an end of the boom 121 when the boom 121 is at an upper boundary of the disconnect envelope (e.g., boom envelope 208). The position of the warning indicator 216 easily gets the operator's attention when the boom 121 is away from the other indicators. The warning indicator 216 informs the operator when the boom has reached the upper boundary of the boom envelope 208 without having to shift their attention down to the bottom of the display.

In one aspect, the disconnect status indicator 228 indicates that the aerial refueling device was properly disconnected, but the fail status indicator 222 informs an operator that the aerial refueling device 120 is not properly positioned within the boom envelope 208 and, as such, is not ready for use. In another aspect, the "alias fail" text, as displayed by the fail status indicator 222, informs an operator that the control components 122 of the aerial refueling device 120 have steered the boom 121 to a position outside the boom envelope 208. Thus, the operator should counter steer (e.g., fly) the boom 121 to a proper position within the boom envelope 208 (e.g., as shown in FIG. 3A).

Figure 3E:
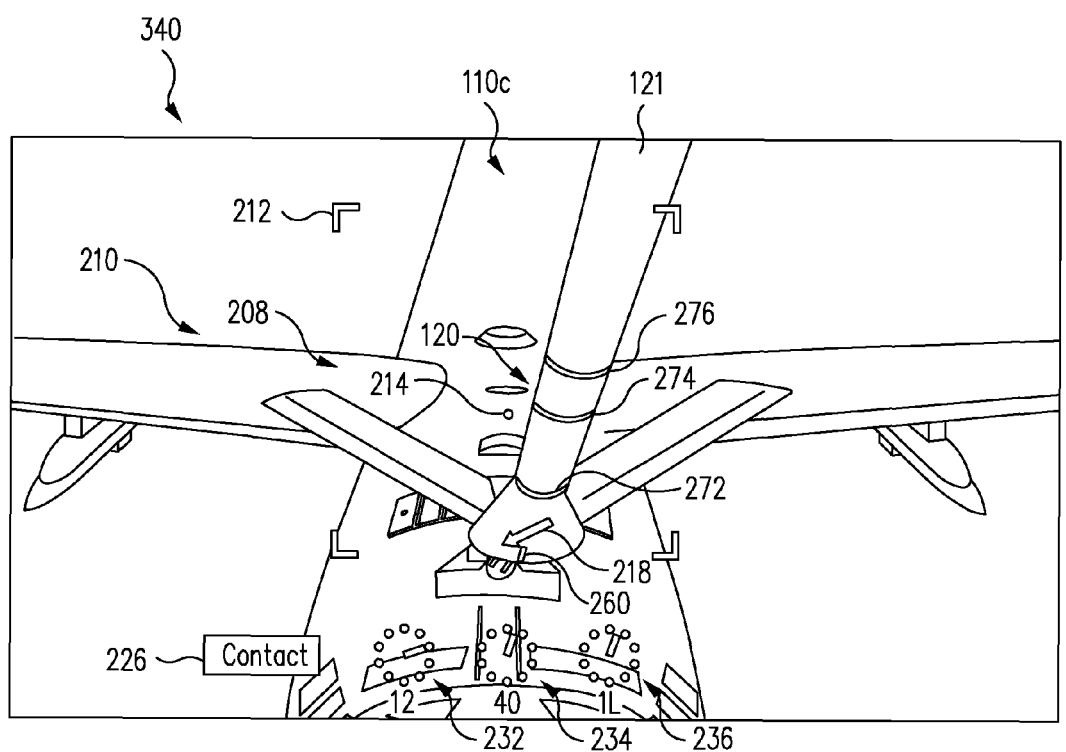

FIG. 3E shows one embodiment of another field of view 340 displaying another photographic image of the aerial refueling device 120, as displayed by the system 160 and seen from an operator in-flight. As shown in FIG. 3E, the field of view 310 includes an image of the receiver aircraft 110c and an image of the aerial refueling device 120 in contact with the receiver aircraft 110c, as indicated by the contact status indicator 226. In one aspect, FIG. 3E shows how the second elevation indicator 274 (e.g., 40° el band) on the boom 121 lines up with the center symbol 214, and the stripe 260 on the boom 121 lines up with the chevrons 212 at the lower portion of the boom envelope 208. As shown in FIG. 3E, the position status indicators 232, 234, 236 at the lower portion of the display do not interfere excessively with the operator's view of the receiver aircraft 110c, when the receiver aircraft 110c is low in the display of the field of view 340.

Figure 4A:
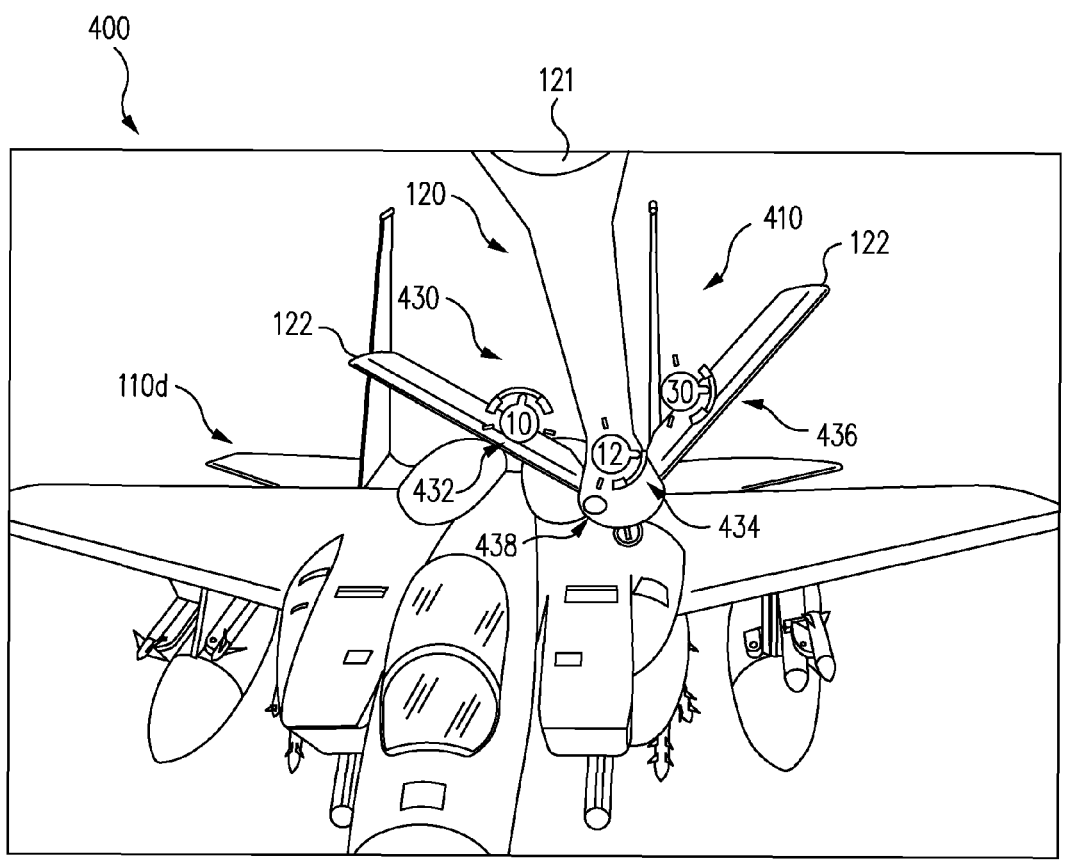
FIGS. 4A-4B show various other exemplary embodiments of an aerial refueling device in various FOV displays having graphic display symbology, in accordance with one or more embodiments of the present disclosure.
Figure 4B:
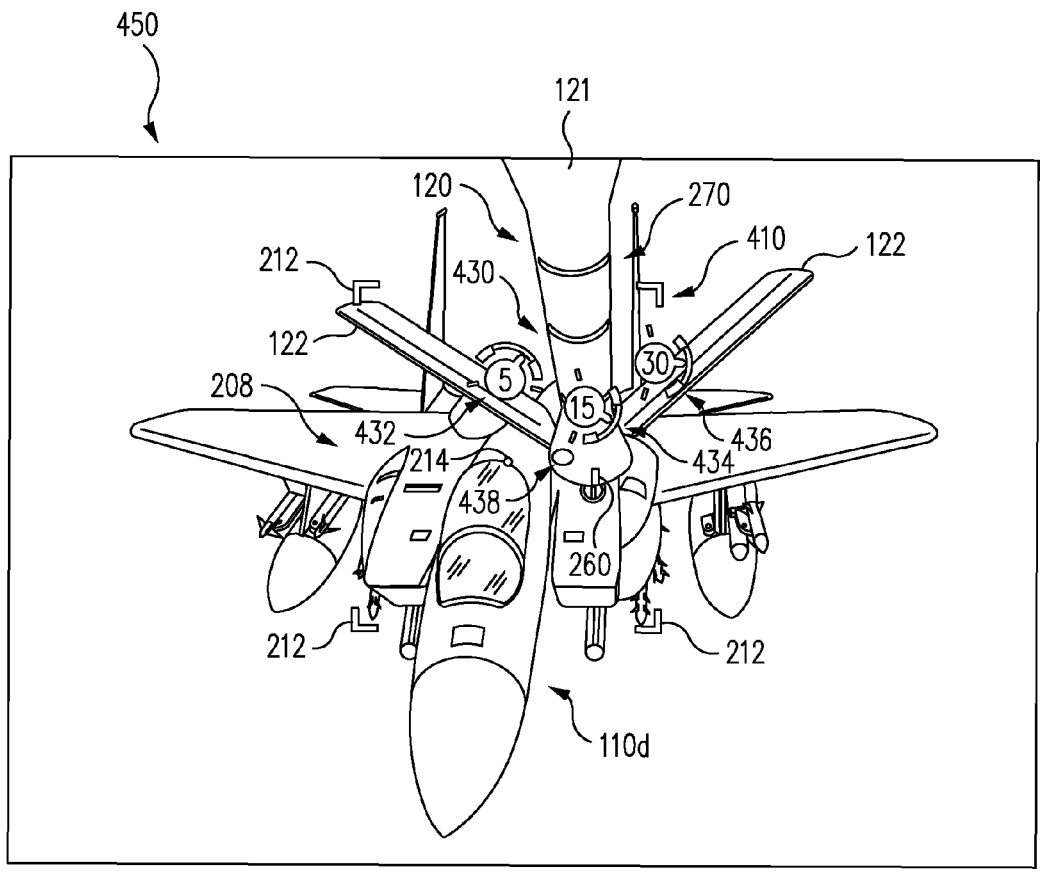

FIG. 4A shows another embodiment of a field of view display 400 having graphic display symbology 410 including a plurality of position indicators 430. FIG. 4B shows still another embodiment of a field of view display 450 having graphic display symbology 410 including the boom envelope 208, the chevrons 212, the center symbol 214, the stripe 260, the one or more elevation indicators 270, the plurality of position indicators 430, and one or more refueling status indicators 438.

In one implementation, as shown on FIGS. 4A and 4B, the position indicators 430 are adapted to be superimposed on portions of the aerial refueling device 120 by tracking the position of the aerial refueling device 121 in the displayed image. As such, the position indicators 430 are adapted to move with the movement of the image of the aerial refueling device 120 as displayed in the field of view 400.

The position indicators 430, as previous described, identify positions of the aerial refueling device 120 and include an elevation position indicator 432, an azimuth position indicator 434, and a telescope position indicator 436. In one implementation, as shown in FIG. 4A, the position indicators 430 are displayed in appearance as analog gauges with a data component (e.g., alphanumeric component) to identify particular degrees of orientation in elevation (el) 232, azimuth (az) 234, and telescope (tel) 236. As shown in FIG. 4A, the position indicators 430 include an indicator arm (e.g., pointer, dial, or hand) that rotates clockwise and/or counter-clockwise to visually indicate the degree of orientation in reference to the data component. In one aspect, the boom envelope boundaries are represented graphically around the indicator arms and may be dynamically adjusted for a type of receiver aircraft and boom telescoping. This arrangement provides an easily viewable indication and image of critical position data and information for steering and maneuvering the aerial refueling device 120 for proper placement relative to the receiver aircraft 110d.

The elevation position indicator 432, in one embodiment, identifies the degree of elevation movement of the boom 121 of the aerial refueling device 120, as described in reference to the vertical or pitch motion of the boom 121 by arrow B in FIG. 1B. In one implementation, as shown in FIG. 4A, the elevation position indicator 432 may be adapted to track the displayed position of at least one of the control components (e.g., wings) 122 of the aerial refueling device 120.

The azimuth position indicator 434, in one embodiment, identifies the degree of azimuth movement of the boom 121 of the aerial refueling device 120, as described in reference to the lateral motion of the boom by arrow A of FIG. 1B. In one implementation, as shown in FIG. 4A, the azimuth position indicator 434 may be adapted to track the displayed position of at least one of the control components 122 of the aerial refueling device 120.

The telescoping position indicator 436, in one embodiment, identifies the degree of axial movement of the boom tip 123 from the boom 121 of the aerial refueling device 120, as described in reference to the telescoping motion of the boom tip 123 by arrow C of FIG. 1B. In one implementation, as shown in FIG. 4A, the telescoping position indicator 436 may be adapted to track the displayed position of an end portion of the boom 121 of the aerial refueling device 120.

The one or more refueling status indicators 438, in various embodiments, provide an indication of a refueling status of the receiver aircraft 110d. As shown in FIG. 4A, the refueling status indicator 438 may be positioned in the field of view 400, such as proximate to a lower portion of the boom 121, e.g., near the boom tip 123 and/or near one or more of the position indicators 432, 434, 436. The refueling status indicator 438 may include an indication of a ready (r) refueling status (e.g., as shown in FIG. 4A), a contact (c) refueling status, and/or a disconnect (d) refueling status. In various implementations, the refueling status indicator 438 may be color-coded in appearance such that a blue background with a white colored character (r) may indicate a ready status, a green background with a black colored character (c) may indicate a connect status, and/or a yellow background with a black colored character (d) may indicate a disconnect status.

In one implementation, a fuel status box (not shown) may be displayed in a portion of the field of view 400. For example, the fuel status box may be displayed within a 30 degree field of view centered on the housing of the control components 122 at the intersection of the boom 121 and control component hinge lines. Also, caution and warning display indications, such as the warning indicator 216 and status indicators 220 of FIG. 2A, may be positioned in the field of view 400 with the intent of facilitating operator recognition of events.

In various implementations, referring to FIGS. 4A and 4B, boom envelope azimuth, elevation, and telescoping boundaries for the receiver aircraft lid are dynamically adjusted for that receiver aircraft type and boom telescoping. The background color of the gauges 432, 434, 436 coincide with position of the boom 121 relative to the boom envelope 208. Status indicators are overlaid on the housing of the control components 122, and in this case, they include routine boom state information. All of the indicators move with the boom 121. Filters may be used to reduce jitter or jumpiness of the indicators as a result of noise in the boom position measurements, and to ensure that the symbols remain readable during rapid boom movement. As the boom moves to a boundary of the visual field of view of the display, the overlaid symbology remains visible at the edge of the display, ghosting the position of the boom 121.

Referring to FIG. 4B, boom markings reference overlays as described in FIG. 2B, which are combined with the symbology anchored to the boom 121. This concept provides intuitive analog boom position references with the concentrated information superimposed on the boom 121. Besides providing a reference for boom position, the chevrons 212 provide an operator with known references in the field of view that aid in judging the distance to the receiver aircraft 110c as the receiver aircraft 110c approaches the tanker aircraft 100.

Figure 5:
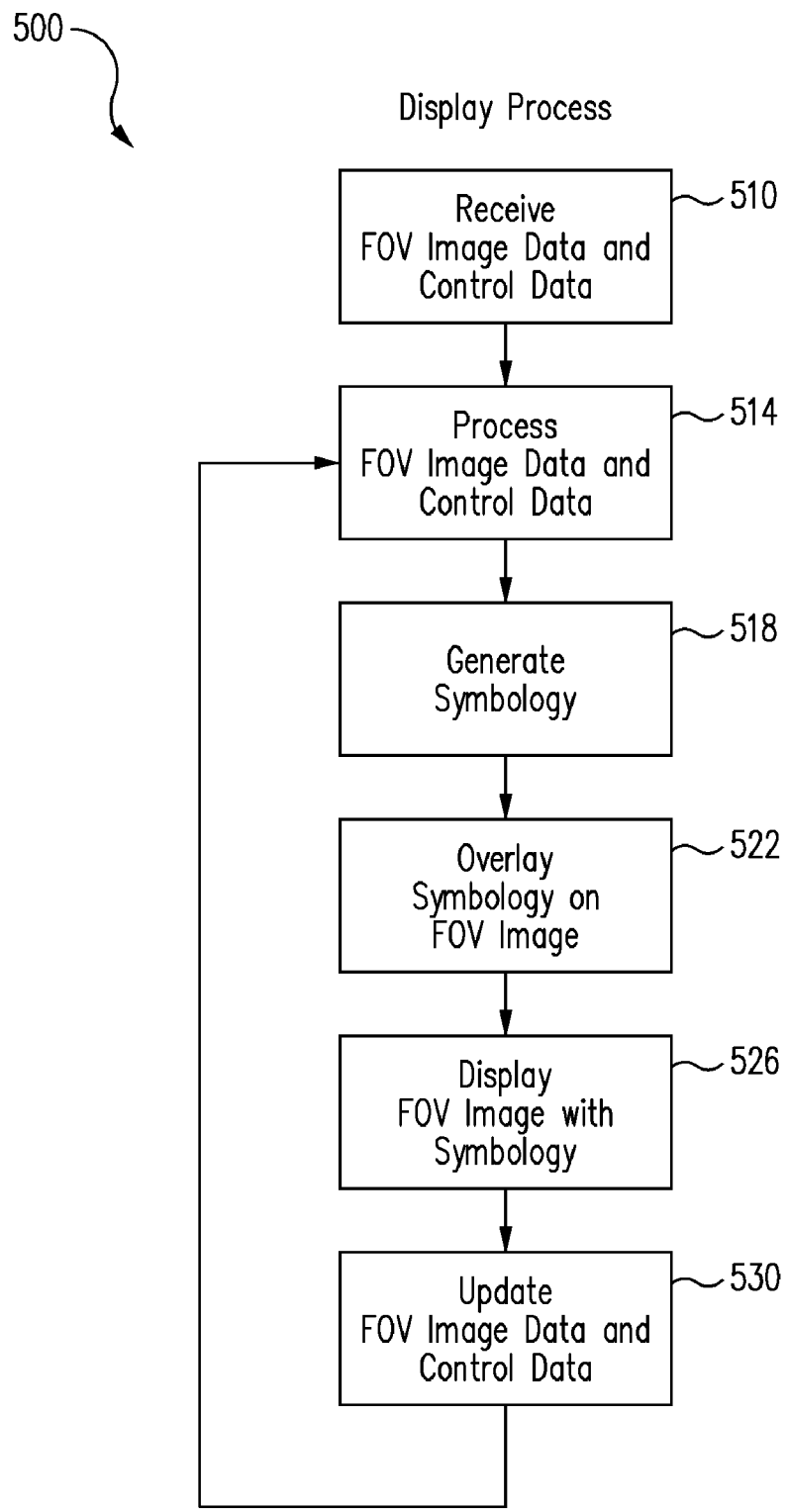
FIG. 5 shows one embodiment of a process for facilitating FOV displays having graphic display symbology, in accordance with an embodiment of the present disclosure.

FIG. 5 shows one embodiment of a process 500 for facilitating the display of a field of view (FOV) having graphic display symbology. The description of FIG. 5 references the visual display system 160 of FIGS. 1A-1D and the FOV displays of FIGS. 2A-4B.

In one implementation, the controller 130 receives FOV image data from the optical sensors 140 including stereoscopic cameras 141 (block 510), and the controller 130 receives control signals from an operator via the operator input device 150 (block 510). Next, the controller 130 processes the received FOV image data and control data (block 514). Next, the controller 130 generates graphic display symbology based, at least in part, on the control data received from the operator input device 150 (block 518). Next, the controller 130 further processes the FOV image data by combining the generated symbology with the FOV image data (block 522). In one aspect, this processing is adapted to display the symbology as overlaid or superimposed on the FOV image data. Next, the controller 130 displays the FOV image with the symbology in the display component 153 for viewing by an operator (block 526). Next, the controller 130 updates the FOV image data from the optical sensors 140 and the control signals from the operator input device 150 (block 530). Next, the process 500 returns (or loops back) to block 514 so that the controller 130 may process the updated FOV image data and the control data. The process 500 continues therefrom.

In various implementations, the controller 130 may be adapted to store optical sensor data, FOV image data, and control signal data in a storage component, without departing from the scope of the present disclosure. The controller 130 may also be adapted to retrieve these various types of data and information related thereto from the storage component.

Figure 6:
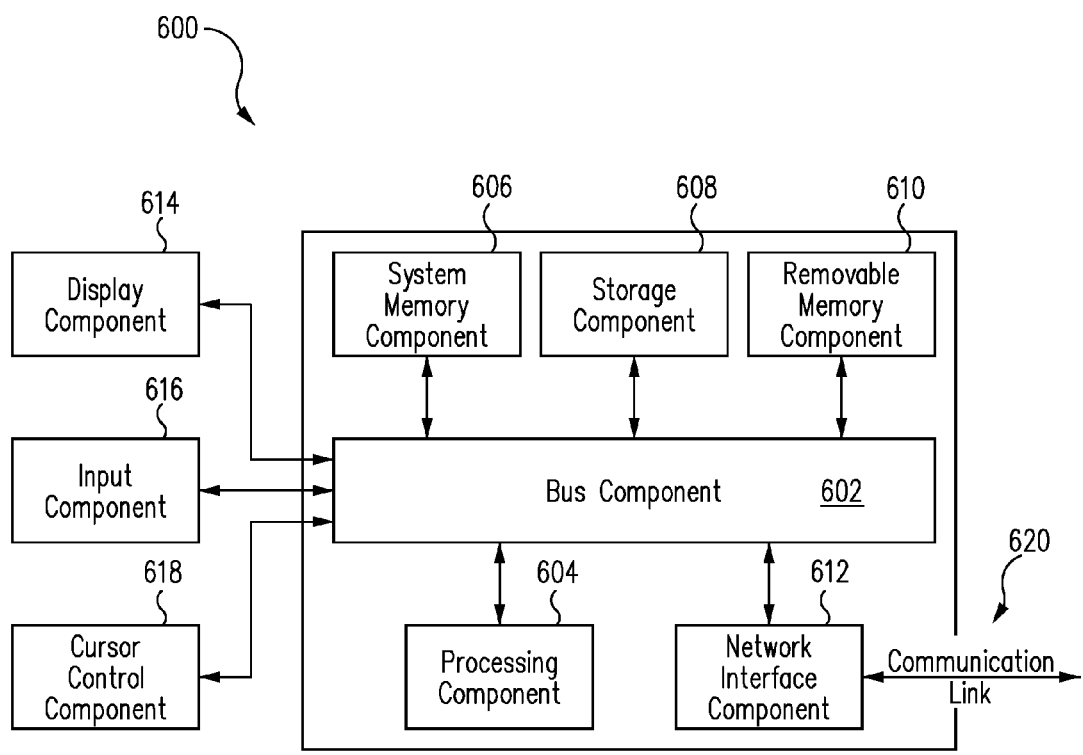
FIG. 6 is a block diagram of a computer/controller system suitable for implementing one or more embodiments of the present disclosure.

FIG. 6 is a block diagram of a computer system and/or controller 600 suitable for implementing embodiments of the present disclosure. Computer system 600 includes a bus 602 or other communication mechanism for communicating information, which interconnects subsystems and components, such as processor 604, system memory component 606 (e.g., RAM), static storage component 608 (e.g., ROM), removable memory component 610 (e.g., removable ROM memory, such as EEPROM, smart card, flash memory, etc.), wired or wireless communication interface 612 (e.g., transceiver, modem or Ethernet card), display component 614 (e.g., LCD, CRT, etc.), input component 616 (e.g., sensors, such as optical sensors including stereoscopic cameras, keyboard, microphone, touch screen on display), and cursor control component 618 (e.g., mouse button).

In accordance with embodiments of the invention, computer system 600 performs specific operations by processor 604 executing one or more sequences of one or more instructions contained in system memory component 606. Such instructions may be read into system memory component 606 from another computer readable medium, such as static storage component 608 or removable memory component 610. In other embodiments, hard-wired circuitry may be used in place of or in combination with software instructions to implement the invention.

Logic may be encoded in a computer readable medium, which may refer to any medium that participates in providing instructions to processor 604 for execution. Such a medium may take many forms, including but not limited to, non-volatile media, volatile media, and transmission media. In various implementations, non-volatile media includes removable storage media, such as removable memory component 610, volatile media includes dynamic memory, such as system memory component 606, and transmission media including wireless transceivers. In one example, transmission media may take the form of radio waves, such as those generated during radio wave and infrared data communications.

Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read.

In various embodiments of the invention, execution of instruction sequences to practice the invention may be performed by computer system 600. In various other embodiments of the invention, a plurality of computer systems 600 coupled by communication link 620 (e.g., wireless cell phone network, wireless or wired LAN, PTSN, or various other wireless networks) may perform instruction sequences to practice the invention in coordination with one another.

Computer system 600 may transmit and receive messages, data, information and instructions, including one or more programs (i.e., application code) through communication link 620 and communication interface 612. Received program code may be executed by processor 604 as received and/or stored in removable memory component 610 or some other non-volatile storage component for execution.

Where applicable, various embodiments of the invention may be implemented using hardware, software, or various combinations of hardware and software. Where applicable, various hardware components and/or software components set forth herein may be combined into composite components comprising software, hardware, and/or both without departing from the scope and functionality of the present disclosure. Where applicable, various hardware components and/or software components set forth herein may be separated into sub-components having software, hardware, and/or both without departing from the scope and functionality of the present disclosure. Where applicable, it is contemplated that software components may be implemented as hardware components and vice-versa.

Software, in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, ordering of various steps described herein may be changed, combined into composite steps, and/or separated into sub-steps to provide features described herein.

Embodiments described above illustrate but do not limit the disclosure. It should also be understood that numerous modifications and variations are possible in accordance with the principles of the present disclosure. Accordingly, the scope of the disclosure is defined only by the following claims.

What is claimed is:

1. A system for in-flight fuel delivery, the system comprising:
    an aerial refueling device adapted to provide fuel to a receiver aircraft;
    an optical component adapted to capture images of the aerial refueling device and the receiver aircraft;
    an operator input component adapted to interface with an operator and capture control signals as input from the operator;
    a display component adapted to display images; and
    a controller adapted to receive the captured images and the captured control signals, process the control signals by generating graphic display symbology, process the images by generating a combined image having the generated graphic display symbology superimposed on the images, and display the combined image on the display component for viewing by the operator,
    wherein the controller is adapted to superimpose the graphic display symbology on a portion of the images obscured by the aerial refueling device.

2. The system of claim 1, wherein the controller is adapted to dynamically position the graphic display symbology over the portion of the images obscured by the aerial refueling device as the aerial refueling device moves in the images.

3. The system of claim 1, wherein the aerial refueling device includes a boom component and at least one rudder component, and wherein the aerial refueling device includes physical markings on a portion of at least one of the boom component and the at least one rudder component.

4. The system of claim 3, wherein the controller superimposes the graphic display symbology on a portion of the image proximate to the physical markings on the aerial refueling device.

5. The system of claim 1, wherein the optical components comprise stereoscopic cameras adapted to have a field of view of at least one of the aerial refueling device and the receiver aircraft, and wherein the graphic display symbology is superimposed over the image in the field of view.

6. The system of claim 1, wherein the graphic display symbology includes a plurality of chevron symbols that define a boom envelope in the image, and wherein the chevron symbols are positioned at corners of the boom envelope, and wherein the graphic display symbology includes a center symbol positioned at a center of the boom envelope.

7. The system of claim 1, wherein the graphic display symbology includes a plurality of position indicators that provide position information related to the aerial refueling device including at least one of an elevation position of a boom component of the aerial refueling device, an azimuth position of the boom component of the aerial refueling device, and a telescoping position of a boom tip component of the aerial refueling device.

8. The system of claim 7, wherein the position indicators include multi-dot circles with a rotating arm that are utilized for numeric scales.

9. The system of claim 1, wherein the graphic display symbology includes warning indicators and status indicators that are displayed in the image with a semi-transparent pixel mask to avoid obscuring the aerial refueling device or the receiver aircraft.

10. The system of claim 1, wherein the graphic display symbology includes a force cue comprising an arrow superimposed on a portion of the aerial refueling device, and wherein the arrow defines a direction of projected force on a nozzle component of the aerial refueling device.

11. The system of claim 1, wherein the graphic display symbology includes a master caution indicator and a master warning indicator superimposed on a portion of the aerial refueling device, and wherein the master caution indicator comprises a yellow color to indicate a master caution state, and wherein the master warning indicator comprises a red color to indicate a master warning state.

12. The system of claim 1, wherein the aerial refueling device includes a boom component, a boom tip component, and a plurality of rudder components, and wherein the graphic display symbology includes graphic position gauges that track the position of at least one of the boom component and the rudder components in the images.

13. The system of claim 12, wherein the graphic position gauges provide position information related to the aerial refueling device including at least one of an elevation position of the boom component, an azimuth position of the boom component, and an extension position of the boom tip component.

14. A method for in-flight fuel delivery from a tanker aircraft to a receiver aircraft via an aerial refueling device, the method comprising:
receiving images from an optical component, the images having a field of view of at least one of the aerial refueling device and the receiver aircraft;
receiving control signals from an operator input component;
processing the control signals by generating graphic display symbology;
processing the images by generating a combined image having the generated graphic display symbology superimposed on the images; and
displaying the combined image on a display component, wherein the graphic display symbology is superimposed on a portion of the images obscured by the aerial refueling device.

15. The method of claim 14, wherein processing the images includes dynamically positioning the graphic display symbology over the portion of the images obscured by the aerial refueling device as the aerial refueling device moves in the images.

16. The method of claim 14, wherein the graphic display symbology is superimposed on a portion of the image proximate to one or more physical markings on the aerial refueling device.

17. The method of claim 14, wherein the graphic display symbology includes a plurality of chevron symbols that define a boom envelope in the image, and wherein the chevron symbols are positioned at corners of the boom envelope, and wherein the graphic display symbology includes a center symbol positioned at a center of the boom envelope.

18. The method of claim 14, wherein the graphic display symbology includes a plurality of position indicators that provide position information related to the aerial refueling device including at least one of an elevation position of a boom component of the aerial refueling device, an azimuth position of the boom component of the aerial refueling device, and a telescoping position of a boom tip component of the aerial refueling device.

19. The method of claim 18, wherein the position indicators include multi-dot circles with a rotating arm that are utilized for numeric scales.

20. The method of claim 14, wherein the graphic display symbology includes warning indicators and status indicators that are displayed in the image with a semi-transparent pixel mask to avoid obscuring the aerial refueling device or the receiver aircraft.

21. The method of claim 14, wherein the graphic display symbology includes a force cue comprising an arrow superimposed on a portion of the aerial refueling device, and wherein the arrow defines a direction of projected force on a nozzle component of the aerial refueling device.

22. The method of claim 14, wherein the graphic display symbology includes a master caution indicator and a master warning indicator superimposed on a portion of the aerial refueling device, and wherein the master caution indicator comprises a yellow color to indicate a master caution state, and wherein the master warning indicator comprises a red color to indicate a master warning state.

23. The method of claim 14, wherein the aerial refueling device includes a boom component, a boom tip component, and a plurality of rudder components, and wherein the graphic display symbology includes graphic position gauges that track the position of at least one of the boom component and the rudder components in the images.

24. The method of claim 23, wherein the graphic position gauges provide position information related to the aerial refueling device including at least one of an elevation position of the boom component, an azimuth position of the boom component, and an extension position of the boom tip component.

25. A system for in-flight fuel delivery from a tanker aircraft to a receiver aircraft via an aerial refueling device, the system comprising:
means for receiving images from an optical component, the images having a field of view of at least one of the aerial refueling device and the receiver aircraft;
means for receiving control signals from an operator input component;
means for processing the control signals by generating graphic display symbology;
means for processing the images by generating a combined image having the generated graphic display symbology superimposed on the images; and
means for displaying the combined image on a display component,
wherein the graphic display symbology is superimposed on a portion of the images obscured by the aerial refueling device.

* * * * *